United States Patent [19]

Silver

[11] Patent Number: 4,717,826

[45] Date of Patent: Jan. 5, 1988

[54] METHOD FOR DETERMINING INTRACELLULAR MINERAL LEVELS

[75] Inventor: Burton B. Silver, Foster City, Calif.

[73] Assignee: Spectro-Scan, Inc., San Bruno, Calif.

[21] Appl. No.: 878,936

[22] Filed: Jun. 26, 1986

[51] Int. Cl.⁴ .......................... H01J 3/14; H01J 3/26; G01N 23/00

[52] U.S. Cl. .................................. 250/307; 250/310; 250/399

[58] Field of Search ................ 250/306, 307, 310, 399

[56] References Cited

U.S. PATENT DOCUMENTS

| | | | |
|---|---|---|---|
| 3,525,863 | 8/1970 | Constantine et al. | 250/399 |
| 3,984,683 | 10/1976 | Larach | 250/306 |
| 4,037,101 | 7/1977 | Okumura et al. | 250/307 |
| 4,439,640 | 3/1984 | Broadhurst | 250/399 |

OTHER PUBLICATIONS

Federation Proceedings, vol. 42, Mar. 1983.
Seelig and Heggtveit, (1974), Amer. J. Clin. Nutrition, 27:59–79.
Abraham, (1977), N. Eng. J. Med. 296:862–863.
Dyckner, (1979), A. Heart J. 97:12–18.
Whang, (1981), Acta. Med. Scand. 647:139–144.
Levine, (1984), N. Engl. J. Med. 310:1253–1254.
Levin, (1985), Cardiovascular Med. Oct.:37–42.
Hook et al., (1985), J. Am. Coll. Nutrition 4:332, Abst. 52.
Magnesium: Experimental and Clinical Research, 4:210–211, (1985), ( B. Silver).

*Primary Examiner*—Bruce C. Anderson
*Attorney, Agent, or Firm*—Townsend & Townsend

[57] ABSTRACT

Intracellular mineral concentrations are obtained from very small tissue samples, such as sublingual tissue smears. The tissue smears are subjected to excitation radiation, typically a scanning electron beam, and mineral analyses may be based on the profile of emitted x-ray fluorescence. A number of correlations are made between various diseased states, susceptibility to diseased states, metabolic status based on the elevated and depressed levels of some or all of the mineral concentrations.

23 Claims, No Drawings

METHOD FOR DETERMINING INTRACELLULAR MINERAL LEVELS

BACKGROUND OF THE INVENTION

1. Field of the Invention

The present invention relates generally to energy dispersive analyses of intracellular mineral concentrations, and more particularly to methods for determining the concentrations of low molecular weight minerals in relatively small tissue specimens and for relating such concentrations to disease and metabolic status.

A variety of low molecular weight minerals, including calcium, phosphorus, potassium, magnesium, sodium, and chlorine, are essential for proper tissue growth, development, and functioning. Heretofore, researchers have attempted to relate serum levels of these minerals to the disease and metabolic status of patients. Serum levels of the minerals, however, are not necessarily reflective of the intracellular concentrations of the minerals at any given time. Indeed, using the methods of the present invention, it is observed that intracellular mineral levels are much more responsive to diseased conditions and other stress factors than are the serum levels of such minerals.

The determination of intracellular mineral concentrations, however, is problematic. Prior art methods, such as atomic absorption, require relatively large tissue samples in order to obtain the desired information. While such samples may be obtained by surgical techniques, such an approach is hardly desirable for routine screening of asymptomatic subjects. Some researchers have attempted to circumvent this problem by employing lymphocytes as a cellular source. The use of lymphocytes, unfortunately, is not generally useful since their intracellular mineral concentrations do not necessarily correspond to those in body tissues, and they have a large nucleus to cytoplasm ratio. Moreover, the status of the lymphocytes is greatly affected by the presence of infection, and the status of the immune response. Moreover, the lymphocyte isolation techniques seem to have an effect on the measured levels of intracellular minerals.

For these reasons, it would be desirable to provide improved methods for measuring the concentrations of intracellular minerals from relatively small tissue samples which may be obtained by non-invasive techniques. It would be further desirable that the method provide highly accurate measurement of the intracellular concentration of all minerals of interest, provide for measurement of an absolute concentration value rather than a ratio of mineral values, and provide information which may be correlated with the disease and metabolic status of the patient undergoing testing.

2. Description of the Relevant Art

Intracellular mineral concentrations have been associated with a number of diseases. Magnesium and other minerals have been related to cardiovascular disease, ischemia, cardiac necrosis, susceptibility to cardiotoxic agents, as well as having an affect on coronary blood flow, blood clotting, and artherogenesis. Seelig and Heggtveit (1974) Amer. J. Clin. Nutrition 27:59–79. Cardiovascular disease and the relationship of minerals identified by serum, blood, and tissue analysis have been reported by many investigators. See, e.g., Abraham (1977) N. Eng. J. Med. 296:862–863; Dyckner (1979) A. Heart J. 97:12–18; Whang (1981) Acta. Med. Scand. 647:139–144; Levine (1984) N. Engl. J. Med. 310:1253–1254; and Levin (1985) Cardiovascular Med. October:37–42. Hook et al. (1985) J. Am. Coll. Nutrition 4:332, Abstract 52, 26th Annual Meeting of the American College of Nutrition and the Fourth International Symposium on Magnesium, describe the use of electron probe microanalysis for the determination of magnesium in peripheral blood mononuclear cells.

The determination of intracellular magnesium/calcium ratios and the relationship of such ratios to patients with diagnosed cardiovascular disease was first reported by the inventor herein in Federation Proceedings, Vol. 42, March 1983, and at the International Symposium on Magnesium and its Relationship to Cardiovascular, Renal, and Metabolic Disorders, Los Angeles, Calif. in February, 1985. The presentation also discussed the changes in calcium and magnesium levels in athletes before and after athletic competition. A paper based on the earlier presentation was subsequently published in Magnesium: Experimental and Clinical Research, 4:210–211, November 1985.

SUMMARY OF THE INVENTION

The present invention provides a non-invasive method for quantitatively measuring intracellular mineral concentrations in tissue specimens, and further provides for correlating such mineral concentrations to patient disease and metabolic status, particularly cardiovascular disease, hypertension, and metabolic bone disorders, such as osteoporosis. Intracellular mineral concentrations are measured by exposing a small tissue sample, which include as few as 1 to 3 cells, to excitation radiation and detecting fluorescence, i.e., radiation emitted as a result of exposing the minerals to the excitation radiation, within certain preselected energy bands. The intensity of fluorescence within each energy band is proportional to the intracellular concentration of a particular mineral, and testing of numerous subjects has allowed correlation of such intracellular mineral concentrations with certain disease and metabolic conditions.

In the specific embodiment, sublingual cells are obtained by scraping and are fixed on an appropriate substrate. The cells are then exposed to the excitation radiation having an energy in the range from about 8 to 12 keV, and the resulting fluorescence measured in a plurality of particular energy bands corresponding to the desired minerals, typically magnesium, calcium, potassium, sodium, chlorine, and phosphorus. A normalized value of the mineral concentration is then obtained by comparing the measured fluorescence with a background fluorescence, typically obtained by measuring emitted radiation at a band free from expected fluorescence peaks. The normalized value is the ratio of the fluorescence within the mineral band to the fluoresence in the band which is expected to be free from peaks.

DESCRIPTION OF THE SPECIFIC EMBODIMENTS

According to the present invention, methods are provided for determining intracellular mineral concentrations, which concentrations are diagnostic of cardiovascular and metabolic status. The methods provide for quantitative measurement of biologically important minerals, including magnesium, calcium, phosphorous, potassium, sodium, and chlorine, and further provide diagnostic guidelines for relating such concentrations to the presence of or susceptibility to cardiovascular disease, hypertension, osteoporosis and periodontal bone boss. The method is suitable for use with very small tissue specimens, such as sublingual tissue smears, but may be used with virtually any source of viable, preferably nucleated, aerobic cells or tissue. The minerals are detected by exposing the cellular sample to excitation radiation, typically a high energy electron beam, and observing the intensity of fluorescence at particular energy bands characteristic of the minerals of interest. By running the tests of the present invention on cardiovascular disease and osteoporosis/periodontal patients, and comparing the results with tests on a population of asymptomatic individuals, intracellular mineral profiles characteristic of cardiovascular diseases, osteoporosis, and periodontal bone loss have been developed.

The present invention relies on examining individual tissue cells obtained from a patient. A variety of cellular sources are suitable, with the major requisite being that the cells be viable, preferably nucleated, and display surface ultrastructure or microvilli. Such cells are normally obtained from biopsies, vaginal smears, sputum, sublingual smears, and the like. Preferred are sublingual smears which are easily obtained and provide cells which are highly characteristic of the patient's overall cellular metabolism. The method of the present invention is also useful for determining intracellular mineral concentrations in serum samples including lymphocytes and erythrocytes. The mineral concentrations in those samples, however, is not thought to be representative of the patient's overall disease or metabolic status.

Sublingual smears are conveniently obtained by briskly scraping the mucous membranes on the floor of the mouth close to the frenulum to obtain recently replaced, nucleated epithelial cells. Prior to scraping, the oral cavity should be rinsed several times with distilled water, and the patient should not have eaten during the hour prior to the test. The spatula used for scraping must be free from trace elements and other materials which will interfere with the electron fluorescence utilized for detecting the minerals of interest (as described more fully hereinafter). The spatula should be rubbed briskly to obtain the necessary cell sample, but not to the point of pain or bleeding.

The cells on the spatula are transferred to a viewing substrate (as described more fully hereinafter), and a smearing motion is used to evenly distribute the cells in a predesignated area. While the smear is still fresh, a mild fixative is dropped onto the cells and allowed to dry. Suitable fixatives should be free of substances which might fluoresce under electron bombardment and interfere with the testing. One suitable fixative is 95% ethyl alcohol and 2.5% carbowax, available from Medical Packaging Corporation, Panorama City, Calif., under the tradename Cytology Fixative. A second suitable fixative is 84.2% isopropyl alcohol, 6.4% polyethyleneglycol, with the remainder being a spray propellant. This fixative is sold under the tradename Spray-Cyte by Clay Adams, Division of Becton-Dickenson, Parsippany, N.J. Once the smear is air dried, it may be stored, transported to a central laboratory for testing, or may be tested immediately.

Viewing substrates must be conductive and free of materials which might interfere with the expected patterns of fluorescence from the cellular minerals. Particularly suitable are high purity carbon slides or planchettes, typically having dimensions of about 1×2 inches. The slides may be prepared from GTA Grade Grafoil ® available from Union Carbide Corp., Danbury, Conn. Usually, a small viewing area will be embossed or otherwise formed on the slide to indicate proper placement of the tissue specimen. The viewing substrates may also be prepared from other materials, such as glass or plastics, but it will be necessary to deposit a conductive layer on the surface to allow for operation of the scanning electron microscope, as described hereinafter.

Detection of the intracellular mineral concentrations depends on bombarding the cellular sample with high energy radiation, typically electrons or x-rays. The energy of this radiation is partly transferred to the atoms of the specimen, including the minerals of interest, and in a portion of the interactions the transferred energy results in fluorescence of secondary radiation, typically x-rays. The x-ray energy lines or bands of fluorescence from a particular atom or element are uniquely characteristic of the particular atom or element. The present invention relies on measurement of the fluorescence within these characteristic x-ray bands in order to determine the concentration of the minerals present in the cells.

The energy source must possess sufficient energy to excite the biological minerals of interest, and must also be focusable since it is desired to excite single cells without the excitation of surrounding cells. The use of electron beam or x-ray radiation generally meets these requirements.

A further requirement of the present invention is that the cells be visualized during the testing. Such visualization allows the individual cells to be scanned so that viable, non-damaged cells can be selected for excitation. Because of the requirement of visualization, it has been found particularly convenient to employ commercially available scanning electron microscopes in performing the method of the present invention. Such microscopes provide electron beams having energies in the range of interest from 8 to 12 keV, provide for focusing the electron beams, and further provide for visualization of the cellular sample at a variety of magnifications.

The present invention also requires a system for detecting the fluorescence which is emitted from the tissue cells as they are bombarded with the electron excitation radiation. The detection system should provide for discrimination within the energy bands of interest, typically from about 500 to 5000 KeV. Suitable detectors include silicon-lithium detector tubes available commercially from a number of suppliers, including Princeton Gamma Tech, Princeton, N.J.

The emission bands observed fall generally in the range from about 500 to 5000 KeV, with the particular bands chosen to be free of interference from other sources. Emission bands corresponding to the six minerals of interest, together with two background emission bands which were selected to be free of emissions under the conditions of the present test, are set forth in Table 1. In general, the method of the present invention calls for integrating emission counts from the tissue sample in each of the desired emission bands for a predetermined period of time. Such emissions, when compared to the background emissions as will be described in more detail hereinbelow, may be related directly to the absolute mineral concentration in a single cell. Usually, a number of individual cells will be tested and the cellular concentration is taken to be the average.

TABLE 1

| Element | Band Limit (keV) | |
| --- | --- | --- |
| | Broad | Narrow |
| Background | 680–810 | 687.5–802.5 |
| Magnesium | 1170–1330 | 1179.8–1324.2 |
| Phosphorus | 1900–2090 | 1935.1–2088.9 |
| Sodium | 2220–2390 | 2227.3–2384.7 |
| Chlorine | 2530–2710 | 2539.5–2700.5 |
| Potassium | 3220–3400 | 3227.6–3396.4 |
| Calcium | 3600–3780 | 3603.5–3776.5 |
| Background | 4100–4250 | 4100–4250 |

After the desired tissue specimen is mounted and fixed on the carbon slide, the carbon slide may be placed in the specimen holder of the scanning electron microscope, and a working vacuum established in the sample chamber. It has been found that the relative angle of the sample to the electron beam has an effect on the visualization and excitation of the individual cells. It is preferred that the angle of incidence between the electron beam and the carbon slide be reduced to below about 60°, preferably below about 50°, more preferably below about 30°. The lower angle of incidence appears to improve the emission of secondary electrons which produce both the visual image and induce x-ray fluorescence. Moreover, the angle appears to maximize penetration of the electrons through the entire cell, assuring that the entire mineral concentration is observed. Using a conventional electron microscope having a vertical electron beam, the angle of incidence may be reduced by tilting the specimen holder upward from the horizontal.

Once the slide holding the cellular specimen is in place and the vacuum drawn, the microscope is turned on with the magnification in the range from about 250 to 300 times, which will usually reveal about several hundred individual cells. The user should select cells which are nucleated, undamaged, and display microvilli or have discrete membrane ultrastructure. After selecting one such cell, the magnification is increased until only that cell appears in the visualization screen of the microscope. Because of the nature of the microscope, the scanning area of the electron beam has been reduced to that single cell, and the incident radiation is not falling on other cells on the slide.

Once the single cell has been focused upon, the x-ray fluorescence detector is turned on and the emitted radiation pattern observed for a preselected magnification time, typically about 100 seconds. The detector is connected to a counter, typically a computer controlled counter, which records the radiation counts in each energy band of interest. Thus, after the preselected test period, a measure of the total emission in each band has been made. This process will be repeated for a desired number of cells, typically in the range from 10 to 100, more typically in the range from 15 to 25. Once all the data are accumulated, the averages for the energy emission per cell are calculated. After obtaining the average energy emission in each energy band of interest, including the background energy bands, it is necessary to calculate the mineral concentration within the cells.

Because of the nature of the system, it is possible to directly calculate concentrations in conventional units, such as Meq/L. Using calibrated individual standards for comparison, it is possible to directly calculate concentrations utilizing the same conditions during measurement, e.g., mass per cell or volume, as follows:

$$C = \frac{SP}{STD} (Meq(STD))$$

where:
C = Unknown mineral concentration.
SP = Specimen counts.*
STD = Standard counts.*
Meq(STD) = Standard mineral concentration.

* Following normalization of standard to unknown by subtraction of background.

Alternatively, the present invention can employ arbitrary concentration units which are defined as fluorescence counts per unit volume, where the unit volume is taken to be the volume of a single cell, approximately 800 $\mu m^3$.

Voltage control of the electron gun in the electron microscope is controlled in the range from about 5 to 15 keV, preferably about 8 to 12 keV, which corresponds to the excitation range of the biological minerals of interest. Higher voltages would stimulate x-rays from heavier elements more readily and would fail to efficiently stimulate the lighter elements, such as sodium and magnesium. Voltages lower than 5 keV would not be able to adequately excite the heavier biological minerals. Conveniently, an excitation voltage of 12 keV has been selected. It should be noted that changing the excitation voltage would require recalibration of the system.

In performing the method of the present invention, the emitted energy detector should be located as closely as possible to the cell smear on the tissue slide, in order to capture as high a portion of the emitted x-rays as possible. The detector is preferably located within 50 millimeters of the sample, more preferably within 20 millimeters of the sample, and most preferably within 10 millimeters or less of the sample. The angle of the detector relative to the plane of the slide is not critical, with an angle of about 60° having been found suitable, with 90° being preferred. It should be noted that once any of these parameters are changed, the system will require recalibration. More importantly, the data on cardiovascular and metabolic status, set forth hereinafter, relates only to a particular system having a particular configuration. Once the system is changed in any substantial manner, the data must be corrected to reflect for such changes.

Using the method of the present invention as just described, large groups of patients suffering from cardiovascular diseases and osteoporosis have been screened to determine the intracellular concentrations of magnesium, calcium, potassium, sodium, chlorine, and phosphorus. By comparing the concentrations observed in diseased patients with those found in an equally large number of apparently healthy, asymptomatic control subjects, a range of optimal and suboptimal mineral concentrations have been derived. Such ranges are set forth in Table 2.

TABLE 2

| Mineral | Optimal Range* | Sub-Optimal Range* |
| --- | --- | --- |
| Magnesium | 800–1000 | 600–800 |
| Calcium | 50–80 | 80–200 |
| Potassium | 100–400 | 50–100 |
| Sodium | 10–14 | 14–30 |
| Chlorine | 11–25 | 25–50 |
| Phosphorus | 900–1200 | 1200–2100 |

*Units of fluorescent intensity (peak/background)/cell volume (800$\mu^3$).

The units set forth in Table 2, of course, are specific to the equipment employed in screening the patient and control subjects. The pattern of identifying depressed levels of magnesium and potassium as well as elevated levels of calcium, sodium, chlorine and phosphorus in correlating these two particular disease states, however, is universal and would apply to any system employed. Particular disease relationships thus far uncovered are set forth in Table 3.

TABLE 3

| Disease | Mg | Ca | K | Na | Cl | P |
|---|---|---|---|---|---|---|
| Cardiovascular Disease | D | E | D | E | N | E |
| Hypertension | D | E | D | E | N | E |
| Osteoporosis/ Periodontal Bone Loss | D | E | E | N | E | E |

D - Depressed
E - Elevated
N - Normal

The present invention is particularly useful as a screening method to identify patients having susceptibility to cardiovascular disease and/or osteoporosis. Using the methods of the present invention, cellular mineral profiles for the patient may be obtained and compared with the indications of Table 3, or with future correlations made using the mineral analysis technique. When the patient is found to display risk factors in any of the mineral concentrations, and particularly in the magnesium, calcium, potassium, and phosphorus concentrations, further diagnostic measures can be taken to discover whether the patient is in fact at risk for cardiovascular disease, hypertension, osteoporosis, and/or periodontal bone loss.

The following experimental results are offered by way of illustration, not by way of limitation.

EXPERIMENTAL

Materials and Methods

1. Sublingual cell smears were obtained from human subjects after thorough rinsing of the sublingual area with distilled water. A chemically clean wooden spatula was used to vigorously scrape the cells and smear them on a pure carbon slide substrate. While still wet, the smears were fixed using either a liquid cytology fixative from a disposable envelope or cytology spray fixative, as described above. The slides were allowed to air dry and then examined in a scanning electron microscope (International Scientific Instruments, Santa Clara, Calif., Model IIIA) for size, distribution, and cellular features, i.e., nucleus, cell membrane elements, flat position and overlap). The angle of incidence of the electron beam was 55°, and the fluoresced x-rays were detected using an energy dispersive x-ray analyzer (Princeton Gamma Tech, System III, Model 3000T) Calculations of the x-ray intensity for each element per cell volume were calculated based on the ratio of peak to background radiation observed for each element in predefined energy bands, as described above. Such peak to background values were then correlated with normal and abnormal conditions by screening large populations of symptomatic and asymptomatic human subjects.

Three healthy, asymptomatic control groups were examined. The first group consisted of eleven age-matched triathletes. The second group consisted of ten mixed individuals with no apparent symptoms of disease. The third group consisted of four mixed individuals with no apparent symptoms of disease, who further showed no symptoms of coronary artery disease (CAD) when tested by intravenous angiography.

Four groups of symptomatic patients were also examined. The first group consisted of eleven patients undergoing cardiac bypass surgery who were diagnosed as having cardiovascular disease by intravenous angiography. The second group consisted of thirty four patients diagnosed as having arteriosclerotic heart disease (ASHD), peripheral vascular disease, and hypertension with and without potassium repletion. The third group consisted of ten patients diagnosed as having atrial fibrillation (AF). The fourth group consisted of sixteen patients diagnosed as having osteoporosis and/or periodontal disease.

RESULTS

Table 4 sets forth the observed intracellular mineral concentrations for the various test and control groups, where the units of concentration are expressed as fluorescence (peak/background)/cell volume ($800\mu^3$).

TABLE 4

| Control or Patient Group | Mineral Concentration | | | | | |
|---|---|---|---|---|---|---|
| | Ca | Mg | P | K | Na | Cl |
| Triathletes | 66.8 ± 2.0 | 806 ± 8.4 | 1208 ± 23 | 109.3 ± 5.8 | 13.3 ± 0.2 | 16.7 ± 1.1 |
| Asymptomatic Mixed | | | | | | |
| Asymptomatic Mixed* | | | | | | |
| Bypass-Angiogram Patients** | 94.3 ± 9.7 | 695 ± 14.8 | 1423 ± 39 | 95.5 ± 9.9 | 11.5 ± 0.5 | 16.1 ± 1.1 |
| ASHD and HTN Patients≠ | 121.4 ± 6.0 | 727 ± 6.8 | 1460 ± 51 | 79.9 ± 3.9 | 12.9 ± 0.5 | 20.4 ± 1.7 |
| Atril Fibrillation Patients≠≠ | 113.4 ± 4.2 | 711.2 ± 9.3 | 1168 ± 37 | 86.7 ± 5.9 | 12.1 ± 0.2 | 19.0 ± 0.8 |
| Osteoporosis and Periodontal bone loss patients | 118.4 ± 10.6 | 730.9 ± 12.5 | 1437 ± 67 | 141.5 ± 20.1 | 12.1 ± 0.3 | 17.1 ± 1.6 |

*Confirmed as free from CVD by angiography.
**On intravenous potassium before and during test.
≠Patients receiving potassium supplements had a mean potassium concentration of 176.9 ± 18.9.
≠≠One patient had intracellular potassium of 620.5.

Patients undergoing by-pass surgery were also evaluated by analyzing freeze dried biopsy material from the right atrial appendate, aortic punch, and saphenous vein taken and frozen during surgery. The same methodology was used to evaluate the biopsy specimens as was used for the sublingual smears. Results indicated high correlation between intracellular ion levels in the sublingual cells and such levels in the surgical samples. Magnesium levels in eleven were 708.8 compared to control values of 806.6 in the sublingual cells. Calcium was elevated in both sublingual cells and atrial tissue as well as aortic tissue. The saphenous veins had control levels of both calcium and magnesium. The patients had been given intravenous potassium and the sublingual potassium and chlorides were in the control ranges as reported above.

In accordance with the subject invention, accurate and sensitive assays are provided for detecting the intracellular concentrations of calcium, magnesium, phosphorus, potassium, sodium and chlorine. Such concentrations have been shown to be diagnostic of bone disorders, cardiovascular disease, and related disorders.

Although the foregoing invention has been described in some detail by way of illustration and example for purposes of clarity of understanding, it will be obvious that certain changes and modifications may be practiced within the scope of the appended claims.

What is claimed is:

1. A method for determining the intracellular concentration of a mineral, said method comprising:
    exposing a tissue specimen to excitation radiation consisting of an electron beam or x-rays at a first preselected energy, said radiation being individually directed at non-damaged cells other than lymphocytes and erythrocytes;
    measuring the intensity of fluorescence from the individual cells of the tissue specimen within at least one energy band characteristic of a particular mineral; and
    determining the intracellular concentration of the mineral by comparing the measured intensity of fluorescence with a measure of background fluorescence at a second energy band.

2. A method as in claim 1, wherein the tissue specimen is a tissue smear.

3. A method as in claim 2, wherein the tissue smear is a sublingual tissue smear.

4. A method as in claim 1, wherein the excitation radiation is directed at a single cell of the tissue specimen.

5. A method as in claim 1, wherein the energy band characteristic of a mineral is in the range from about 500 to 5000 keV.

6. A method as in claim 1, wherein the background fluorescence is measured within an energy band which is substantially free of peaks associated with intracellular minerals.

7. A method for determining the intracellular concentration of a mineral, said method comprising:
    exposing a tissue cell smear to a scanning electron beam of a first preselected energy;
    visualizing individual cells in the smear by means of a secondary electron detector;
    identifying at least one viable individual cell based on predetermined selection characteristics;
    scanning the one viable cell with the electron beam;
    measuring the intensity of fluorescence emitted from the one viable cell within at least one energy band characteristic of a particular mineral; and
    determining the intracellular concentration of the mineral by comparing the measured intensity of fluorescence with a measure of background fluorescence at a second energy band.

8. A method as in claim 7, wherein the tissue cell smear is a sublingual tissue smear.

9. A method as in claim 7, wherein the tissue cell smear is placed in a scanning electron microscope which generates the scanning electron beam and provides for visualization of the cells.

10. A method as in claim 9, wherein the energy of the electron beam generated by the scanning electron microscope is in the range from 8 to 12 keV.

11. A method as in claim 9, wherein the single cell is scanned by focusing the scanning electron microscope on said single cell.

12. A method as in claim 7, wherein the one viable individual cell is selected based on the presence of a nucleus, microvilli, and membrane ultrastructure.

13. A method as in claim 7, wherein the fluorescence characteristic of a mineral is measured by an x-ray detector capable of measuring radiation having an energy in the range from about 500 to 5000 keV.

14. A method as in claim 7, wherein the fluorescence characteristic of a mineral is measured at energy bands selected from the group consisting of from about 1170 to 1330 keV corresponding to magnesium, from about 1930 to 2090 keV corresponding to phosphorus, from about 2220 to 2390 keV corresponding to sodium, from about 2530 to 2710 keV corresponding to potassium, and from 3590 to 3780 keV corresponding to calcium.

15. A method as in claim 14, wherein the background fluorescence is measured at energy bands selected from the group consisting of about 680 to 810 keV and about 4100 to 4250 keV.

16. A method as in claim 7, wherein the intensity of fluorescence is compared to the background fluorescence by calculating the ratio.

17. A method for diagnosing a disease, disease susceptability, or metabolic status, said method comprising:
    exposing individual non-damaged cells of a tissue specimen other than lymphocytes or erythrocytes to excitation radiation consisting of electrons or x-rays at a first preselected energy;
    measuring the intensity of fluorescence from the tissue specimen within a plurality of energy bands characteristic of the intracellular minerals;
    determining the intracellular concentrations of a plurality of cellular minerals by comparing the peak of fluorescence intensity within the plurality of energy bands with measures of background fluorescence at a plurality of secondary energy bands;
    comparing the intracellular mineral concentrations with predetermined normal concentrations to determine a pattern of elevated, depressed, and normal concentrations; and
    diagnosing the disease, disease susceptibility, or metabolic status based on the pattern.

18. A method as in claim 17, wherein the tissue specimen is a tissue smear.

19. A method as in claim 18, wherein the tissue smear is a sublingual tissue smear.

20. A method as in claim 17, wherein the excitation radiation comprises a focused electron beam.

21. A method as in claim 17, wherein the excitation radiation is directed at a single cell of the tissue specimen.

22. A method as in claim 17, wherein the energy bands characteristic of the minerals are in the range from about 500 to 5000 keV.

23. A method as in claim 17, wherein the background fluorescence is measured within an energy band which is substantially free of peaks associated with intracellular minerals.

* * * * *